United States Patent [19]

Schneider et al.

[11] Patent Number: 4,861,586
[45] Date of Patent: Aug. 29, 1989

[54] ANIMAL BAIT

[75] Inventors: Lothar Schneider; Irma Schneider, both of Tüingen, Fed. Rep. of Germany

[73] Assignee: Hartmut Klocke, Weingarten/Baden, Fed. Rep. of Germany

[21] Appl. No.: 33,951

[22] Filed: Apr. 3, 1987

[30] Foreign Application Priority Data

Apr. 3, 1986 [DE] Fed. Rep. of Germany ....... 3611122

[51] Int. Cl.⁴ ............................................. A01N 25/00
[52] U.S. Cl. ...................... 424/84; 424/410; 424/442; 264/234; 264/237
[58] Field of Search ...................... 426/1; 424/84, 410, 424/442; 264/234, 237

[56] References Cited

U.S. PATENT DOCUMENTS 4,650,673 3/1987 Johnston et al. ...................... 424/84

FOREIGN PATENT DOCUMENTS 2317285 10/1974 Fed. Rep. of Germany ........ 424/84
1233115  5/1960 France ................... 424/84
1288000 11/1962 France ................... 424/84
2055941  5/1971 France ................... 424/84
8601076  2/1986 PCT Int'l Appl. ................... 424/84
440921   1/1936 United Kingdom ................ 424/84

Primary Examiner—Ellis P. Robinson
Assistant Examiner—P. J. Ryan
Attorney, Agent, or Firm—Spencer & Frank

[57] ABSTRACT

A prefabricated animal bait containing a carrier substance and a pharmaceutically active substance, for example, a vaccine against rabies. The carrier substance contains a fat component and an additive to stabilize the shape retention of the bait, with both components being selected in such a manner that the mixture is pasty for processing and does not break in the temperature range in which it will be used. The bait is produced in such a manner that, in a deep-drawn mold, the carrier substance completely surrounds, and envelopes a preassembled unit of the active substance so that the bait merely needs to be pressed out of this carrier foil when it is to be used. Economical industrial production of prefabricated bait in a simple manner, easily and optimally adaptable to the respective animal species and its habitat with respect to temperature and moisture is provided. A particular simlification results from the use of fish meal as the additive since it simultaneously acts as a lure.

20 Claims, 1 Drawing Sheet

ANIMAL BAIT

FIELD OF THE INVENTION

The present invention relates to a prefabricated animal bait containing a pharmaceutical substance, for example a vaccine against rabies.

TECHNOLOGY REVIEW

It is known to administer a pharmaceutical substance to an animal by mixing the active substance in an inert carrier.

The carrier substance, which essentially serves to attract the type of animal to be treated, has in the past been taken itself from animals or parts of animal bodies. For example, chicken heads prepared as bait containing, for example, a vaccine against rabies, may be laid out in the area affected to orally immunize foxes against rabies. When the chicken heads are ingested, the rabies vaccine reaches the mucous membranes in the fox's mouth and is there absorbed.

The preparation of such bait made of animal parts is, however, relatively expensive. This method is therefore uneconomical to use for actions which must be taken over a large area, such as, for example, animal vaccinations.

In several states of the Federal Republic of Germany tests have been conducted with prefabricated bait in which the active substance is embedded in a carrier substance instead of chicken heads.

SUMMARY OF THE INVENTION

The invention provides a prefabricated animal bait containing a pharmaceutically active substance, such as, for example, a vaccine against rabies, enveloped within a carrier including a fat component and an additive to stabilize the shape retention of the bait, with both components being selected in such a manner that the mixture is pasty for processing and does not break in the temperature range in which it will be used.

It is an object of the invention to prepare an improved prefabricated bait which may be manufactured on a large scale with the use of economical carrier substances.

A feature of the invention is to provide a carrier substance for a prefabricated animal bait which is exceptionally stable in the environment, i.e. is resistant to the influence of temperature and moisture in the area in which it will be used.

DETAILED DESCRIPTION OF THE INVENTION

Figures 1, 2:
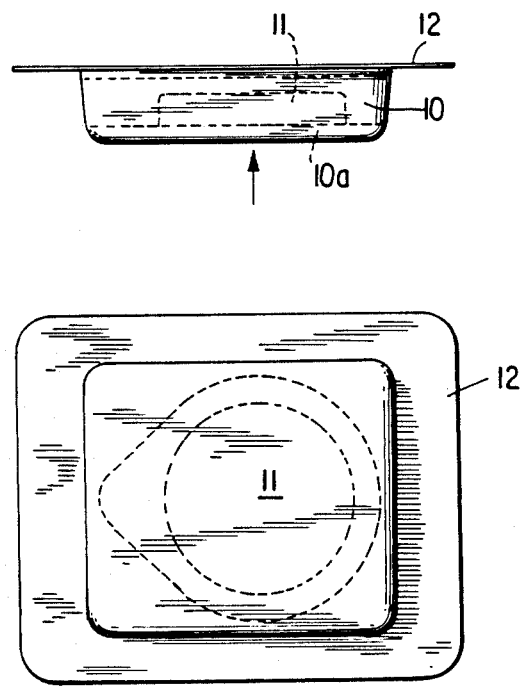
FIG. 1 illustrates a side view of the prefabricated animal bait of the invention.
FIG. 2 illustrates a top view of the prefabricated animal bait of the invention.

The present invention provides a carrier substance including a fat component which has a melting point between 20° and 60° C. and at least one additive to stabilize the shape retention of the bait. The relative proportions of the fat component/additive mixture are selected so that the mixture can be processed in pasty form and will not break in the temperature range in which it is used. The carrier substance contains at least one specific attracting substance.

The selection of a mixture of a fat component and an additive for stabilization, as provided by the invention, permits, on the one hand, easy processing of the mixture above the melting point of the fat component (pasty) and, on the other hand, ensures that, upon cooling of this mixture after manufacture of the bait, the bait hardens and retains its shape within the temperature range thereafter to be encountered in use. In particular, the animal bait does not become brittle, i.e. will not break apart or crumble when the animal to be baited bites it. This carrier substance contains a species specific attracting substance or lure so that the carrier substance as the "artificial bait" constitutes a very attractive "package" for the animal species to be baited and entices it to pick up the bait and bite into the carrier substance so that then the active substance is taken up and absorbed into the mucous membranes of the mouth of the respective animal.

Advantageously, the carrier substance, in the form of a envelope, completely encloses the separately packaged unit containing the pharmaceutically active substance. Such a prefabricated bait is particularly easy to manufacture if the carrier substance and the active substance are accommodated in a mold in which they can be pressed. This may be, in particular, a cup-like deep-drawn mold out of which the prefabricated bait can be pressed in the form of tablets by pressure on the bottom of the deep-drawn cup.

A preferred carrier substance includes a vegetable or animal fat as the fat component and includes fish meal which simultaneously constitutes the additive and the lure. The fish meal together with the fat meets the above-described requirements and additionally constitutes a very strong lure.

A wax-containing further additive may be contained in the carrier substance as a protection against moisture. This wax-containing additive, for example paraffin, protects the prefabricated bait against the influence of moisture which could cause the carrier substance to become soft and thus the bait to become less effective. A wax-containing additive, moreover, produces a protective coating on the mixture which results in an extension of the effective shelf life of the bait. A wax-coating additive also permits further control of the consistency of the fat/additive mixture so that the mixture is pasty during processing and stable in the temperature range at which it will be used.

Thus, the prefabricated bait according to the invention can easily be "set" to the species of animal in question and to its specific environment, by suitable selection of the components of the carrier substance, particularly with respect to the temperatures to be expected. To determine the acceptance of the bait by the particular species of animal, it is easy to apply markers to the carrier substance which may later be detected and permit conclusions as to the acceptance of the bait.

The bait according to the invention can easily be manufactured industrially. The invention provides process steps in which initially the fat component is liquefied, then the additive is mixed in and this mixture is then cooled to below the inactivation temperature of the pharmaceutically active substance employed, if this is necessary, so as not to endanger the active substance to be inserted later. This pasty mixture is then injected in individual portions into a deep-drawn mold until the bottom of the mold is completely covered and this bottom layer is thick enough to have sufficient stability. Then a pre-assembled unit of the active substance is placed into the bottom of the mold and the mold is filled with the pasty mixture until the active substance is completely covered. Finally the bait is cooled, thus causing the mixture to harden, with the hardening temperature of the mixture being selected, by means of its composition, so that it lies above the temperature range in which the bait will be used. The hardening temperature of the mixture is selected so that the bait retains its shape, without, however, becoming brittle under the temperatures usually encountered in the specific area in which the bait will be used.

The paraffin employed as a protection against moisture is preferably added in liquid form and mixed with the already liquefied fat component and shape retaining additive. The lure substance may also be present in the mixture to which the liquid paraffin is added. If fish meal is employed as the additive, no separate lure is required. For special applications it is also possible, instead of homogeneously distributing the lure in the carrier substance, to mist or spray it on after the bait has been completed.

It is also possible to apply a wax-containing additive, such as, for example, paraffin, after the bait has been completed but then care must be taken that the scent given off by the bait is not adversely influenced thereby. If paraffin is added to the fat component and additive as described above, the paraffin merely produces a coating of these components without the lure being impaired in its attracting.

Gelatin to which a hardener has been added can also be used instead of a fat component in the carrier substance for the bait. Sodium alginate or similar chemical compounds can thus serve as hardening additives.

An embodiment of the bait according to the invention will be described briefly with reference to the drawing figures.

In a deep-drawn cup mold 12, a carrier substance has been introduced to form an envelope 10 which encloses a pre-assembled pharmaceutically active substance unit 11, with this unit 11 resting on the initially sprayed-in bottom 10a of envelope 10. After the carrier substance has been sprayed into mold 12, it hardens and the prefabricated bait can then be pushed out of mold 12 in the form of a tablet by pressure on the bottom of mold 12 (arrow).

Such packages can be economically manufactured in large numbers and thus permit, for the first time, the use of bait in large areas to take effective measures against a wide variety of animal diseases or diseases carried by animals. Compared to prior baits which employ animal parts, manufacturing costs are significantly reduced.

The carrier substance is produced as follows, for example:

A vegetable fat having a melting point of about 35° C. is liquefied over night at 54° C., and paraffin is liquefied at about 75° C.

Fish meal having a maximum grain size of about 100 $\mu$ is used as an additive to retain shape and simultaneously as lure.

Of the liquefied vegetable fat, 5 parts by volume are mixed with 1 part by volume paraffin; 4 parts fish meal are added to the mixture under constant stirring and the mixture is cooled to a temperature between 40° and 43° C. When this temperature range is reached, the filling in of the mold, as described above, begins.

If gelatin instead of the fat component is used as the carrier substance, part of the gelatin powder is heated to 75° C. together with 0.5% to 1.5% of hardening additives and 9 parts of water and is thus liquefied. Nine parts by volume gelatin solution is then mixed with further 9 parts of water and 4 parts of fish meal under constant stirring and the mixture is cooled to abut 40° C. Then the mold can be filled in as described above. There are no significant differences in the manufacturing process between manufacture of the bait containing the fat component in the carrier substance and manufacture of the bait containing gelatin in the carrier substance.

This application is related to our application Ser. No. P 36 11 122.8 filed Apr. 3rd, 1986 in the Patent Office of the Federal Republic of Germany, the entire specification of which is incorporated herein by reference.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

We claim:

1. A prefabricated animal bait, comprising:
  a unit of a veterinary composition for the treatment of an animal disease or a disease carried by an animal, said veterinary composition unit enveloped by
  a carrier comprising a fat material having a melting point between about 20° and 60° C., mixed with at least one additive material to stabilize the shape retention of said bait, and at least one lure for said animal to be baited, said fat material and additive material being selected in a ratio to provide a thick paste at about 20° C. and adapted not to become brittle at temperatures at least as low as 0° C.

2. The prefabricated animal bait set forth in claim 1, wherein said veterinary composition unit is pre-assembled in an amount effective to treat an animal to be baited.

3. The prefabricated animal bait set forth in claim 1, wherein said bait is molded.

4. The prefabricated animal bait set forth in claim 1, wherein said fat material is a vegetable or animal fat.

5. The prefabricated animal bait set forth in claim 1, wherein fish meal is used as the additive and the lure.

6. The prefabricated animal bait set forth in claim 1, wherein a wax-containing further additive is contained in the carrier to protect against moisture.

7. The prefabricated animal bait set forth in claim 6, wherein the wax-containing substance is paraffin.

8. The prefabricated animal bait set forth in claim 1, wherein marking substances are added to the carrier.

9. A process of manufacturing a prefabricated animal bait comprising the following steps:
  (a) liquefying a fat material having a melting point between about 20° and 60° C.;
  (b) mixing in at least one additive material to stabilize the shape retention of said prefabricated animal bait;
  (c) cooling the mixture to form a pasty mixture;
  (d) spraying portions of the pasty mixture into a mold until the bottom of the mold is completely covered;
  (e) placing a unit of a veterinary composition for treatment of an animal disease or a disease carried by an animal into the mold;

(f) filling the mold until the unit of the veterinary composition is completely covered; and (g) cooling the bait to below the hardening temperature of the pasty mixture which lies above the temperature range in which the prefabricated animal bait will be used.

10. Process as defined in claim 9, wherein fish meal having a grain size below 100 μ is used as the additive.

11. Process as defined in claim 9, wherein liquid paraffin is added and mixed in before the additive is mixed with the liquid fat component.

12. Process as defined in claim 9, wherein the lure is added to the mixture composed of fat component/additive.

13. Process as defined in claim 9, wherein the lure is misted or sprayed onto the finished bait.

14. A prefabricated animal bait, comprising:
a unit of a veterinary composition for treatment of an animal disease or a disease carried by an animal, said veterinary composition unit enveloped by
a carrier comprising a gelatin having a melting point between about 20° and about 60° C., mixed with at least one additive material to stabilize the shape retention of said bait, and at least one lure for said animal to be baited, said gelatin and additive material being selected in a ratio to provide a thick paste at about 20° C. and adapted not to become brittle at temperatures at least as low as 0° C.

15. The prefabricated animal bait set forth in claim 14, wherein said veterinary composition unit is pre-assembled in an amount effective to treat an animal to be baited.

16. The prefabricated animal bait set forth in claim 14, wherein said bait is molded.

17. The prefabricated animal bait set forth in claim 14, wherein fish meal is used as the additive and the lure.

18. The prefabricated animal bait set forth in claim 14, wherein a wax-containing material is added to said carrier to protect against moisture.

19. The prefabricated animal bait set forth in claim 18, wherein the wax substance is paraffin.

20. The prefabricated animal bait set forth in claim 14, wherein marking substances are added to the carrier.

* * * * *

UNITED STATES PATENT AND TRADEMARK OFFICE
CERTIFICATE OF CORRECTION

PATENT NO. : 4,861,586

DATED : August 29th, 1989

INVENTOR(S) : Lothar Schneider et al.

It is certified that error appears in the above-identified patent and that said Letters Patent is hereby corrected as shown below:

In the heading under Inventors [75] the inventors' city of residence should read --Tubingen--.

Signed and Sealed this

Twenty-third Day of October, 1990

Attest:

HARRY F. MANBECK, JR.

*Attesting Officer*  *Commissioner of Patents and Trademarks*